United States Patent [19]

Wang et al.

[11] Patent Number: 5,033,473

[45] Date of Patent: Jul. 23, 1991

[54] METHOD FOR DISCRIMINATING PACE PULSE TAILS

[75] Inventors: Jyh-Yun Wang, Newton; Mousa N. Shaya, Waltham, both of Mass.

[73] Assignee: Hewlett-Packard Company, Palo Alto, Calif.

[21] Appl. No.: 426,338

[22] Filed: Oct. 24, 1989

[51] Int. Cl.$^5$ .............................................. A61B 5/04
[52] U.S. Cl. ................................ 128/696; 128/419 PT
[58] Field of Search ................. 128/695, 696, 419 PT, 128/703, 704, 708, 419 D, 419 PG

[56] References Cited

U.S. PATENT DOCUMENTS

| | | | |
|---|---|---|---|
| 4,537,201 | 8/1985 | Delle-Vedove et al. | 128/708 |
| 4,585,001 | 4/1986 | Belt | 128/708 |
| 4,585,004 | 4/1986 | Brownlee | 128/419 PT |
| 4,791,936 | 12/1988 | Suell et al. | 128/419 PT |
| 4,887,609 | 12/1989 | Cole, Jr. | 128/696 |
| 4,892,104 | 1/1990 | Ito et al. | 128/419 PT |
| 4,893,632 | 1/1990 | Armington | 128/708 |

Primary Examiner—Francis Jaworski
Assistant Examiner—George Manuel
Attorney, Agent, or Firm—Richard F. Schuette

[57] ABSTRACT

Disclosed is a method and apparatus for discriminating pace pulse tails generated by signals discriminated from QRS complexes by mathematically ascertaining that the signal following the pace pulse peak has an exponential decay. The invention ascertains whether or not the waveform decays exponentially through application of a mathematical equation.

11 Claims, 12 Drawing Sheets

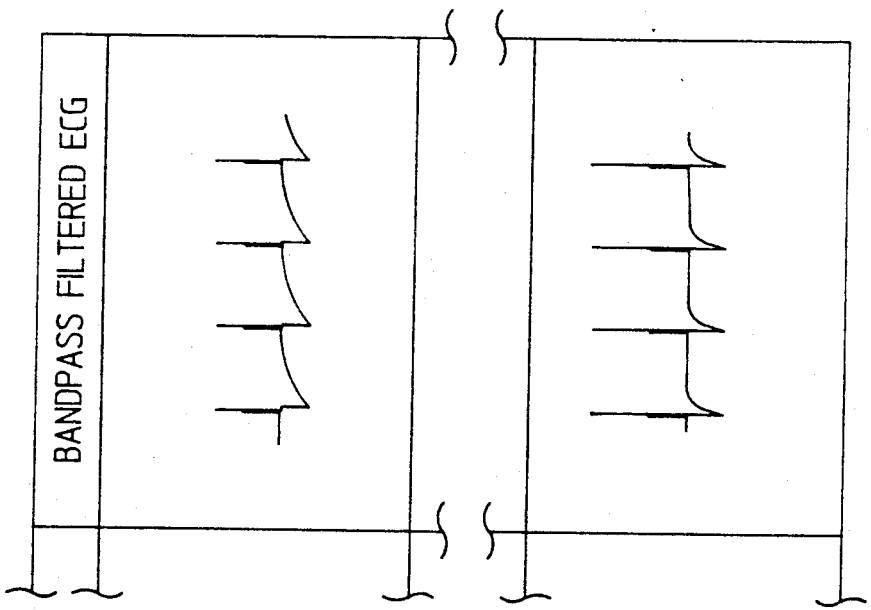
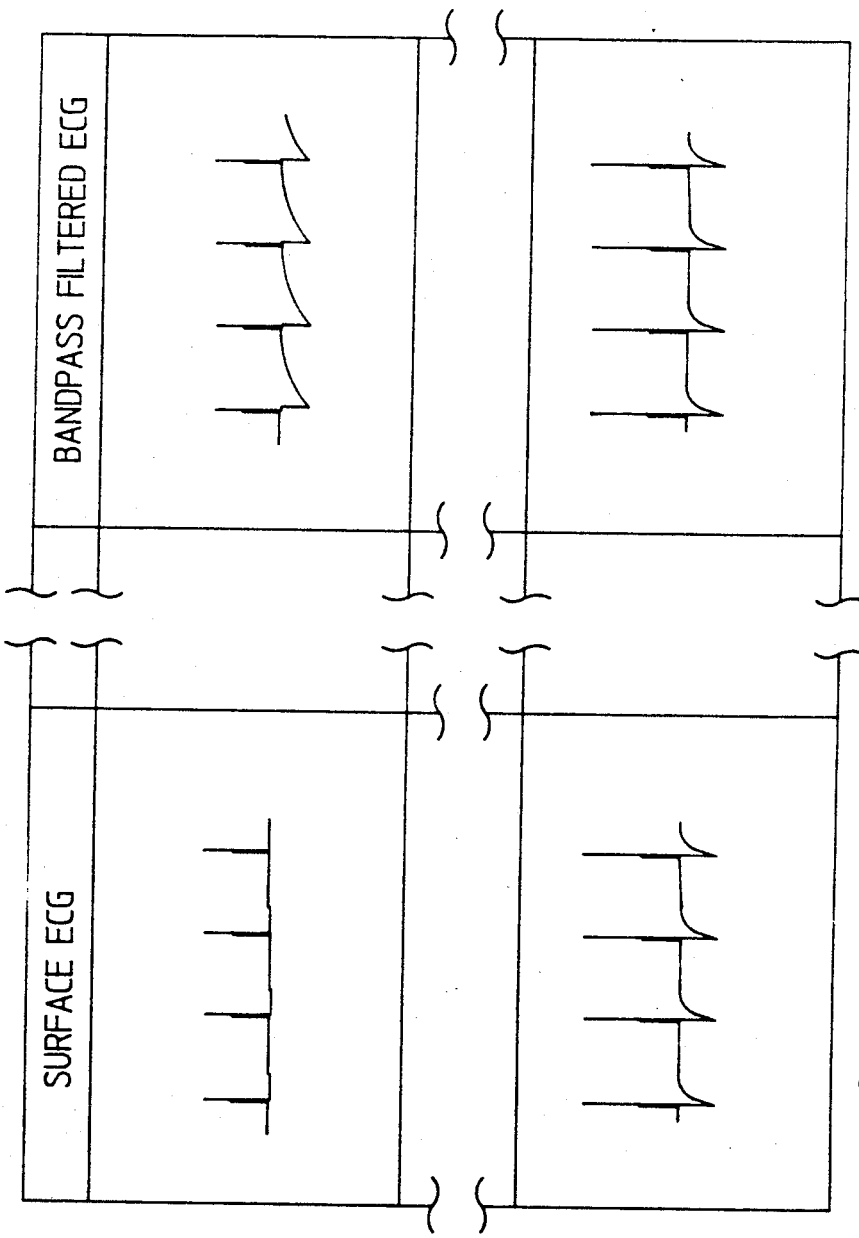

METHOD FOR DISCRIMINATING PACE PULSE TAILS

BACKGROUND OF THE INVENTION

In any Electrocardiogram (ECG) monitoring device, an important feature is the detection and characterization of each individual heart beat present in the ECG signal. This information is then used to generate both heart rate information and alarms in life threatening situations. Monitoring an ECG signal from a patient having a pacemaker is difficult as pace pulses generated by the pacemaker can occur at any time. When they occur between QRS complexes they can be incorrectly detected by a QRS detector and result in an incorrect high heart rate measurement. When they occur during a QRS complex, they can cause incorrect feature measurement and result in an erroneous QRS classification. In particular, the detection of asystole is necessary to alert nurses of the cessation of heart activity which is indicated by the absence of the QRS complex in the ECG signal. However, in the case of patients with pacemakers, the ECG signal, even after asystole, contains periodically occurring pace pulses, which may resemble heart activity. The presence of pace pulses on an ECG signal makes it difficult to detect such asystole conditions.

A typical pace pulse consists of two components, a main pulse and a repolarization pulse. The main pulse, which is used to stimulate the heart, is characterized by its narrow width, sharp rise and fall, and large variation in amplitude. The actual shape of the pace pulse depends on the output coupling design of the pacemaker. The repolarization pulse, sometimes referred to as a pace pulse tail, is used to deplete the capacitive coupling generated by the delivery of the pace pulse charge built up between the heart and the pacemaker. The shape and size of the pace pulse tail is a function of the energy content of the pace pulse and the amount of capacitive coupling. In addition to repolarization, bandpass filtering in the monitoring equipment may create a "pace pulse tail".

Two examples of pace pulse signals recorded on the surface ECG are shown in FIGS. 1A and 1B. FIG. 1A is a pace pulse with a small repolarization tail, whereas FIG. 1B illustrates a large repolarization tail generated by the pacemaker system. As shown in FIGS. 1C, and 1D, both pace pulse signals exhibit significant repolarization tails after bandpass filtering.

In order to more accurately monitor ECG signals it has been found helpful to eliminate pace pulse signals. Such elimination requires that the pace pulse first be identified. The process of identifying pace pulses may employ the technique disclosed in U.S. Pat. No. 4,664,116 and incorporated by reference; wherein, pace pulses are identified by the existence of high frequency "spikes" having narrow width and a sharp rise time which exceeds a minimum dynamic noise threshold.

Additional hardware and software can be employed to remove detected pace pulses (FIG. 3). In particular, a technique is described in U.S. Pat. No. 4,832,041 in which values of the ECG signal that are within a window containing the pace pulse are replaced with substitute values that are an interpolation of selected values of the ECG signal. The substitute values form a line that is very close to what the ECG signal would be if a pace pulse had not occurred. However, this algorithm is not designed to eliminate the pace pulse tail. FIG. 2A shows pace pulse signals with the pace pulse tail, and FIG. 2B illustrates the pace pulse tail after the pace pulse spike has been removed using the above mentioned technique. Unfortunately, the remaining energy of the pace pulse tail may be erroneously detected as a QRS complex. This may cause the misdiagnosis of the patient's underlying ECG rhythm and result in a missed detection of an asystole condition.

Accordingly it is the purpose of this invention to provide a method for differentiating pace pulse tails from true QRS complexes in an ECG signal waveforms.

SUMMARY OF THE INVENTION

In accordance with this invention a method is described by which a paced ECG signal can be analyzed to discriminate pace pulse tails from QRS complexes. Pace pulse tails tend to have an exponential decay which is due to the capacitive discharge of the impulse energy delivered by the pace pulse. Whereas, normal QRS complexes generated by heart muscle contraction do not contain any exponentially decaying segments. By first locating the peak of the pace pulse tail and determining if the signal following the peak decays exponentially, it is possible to identify pace pulse signal tails and discriminate them from QRS complexes.

Since pace pulse tails must follow pace pulses, a detected signal cannot be a pace pulse tail if it is not preceded by a pace pulse. A pace pulse detector can be employed to locate pace pulse signals and a QRS detector, which compares the ECG signal amplitude to a dynamic threshold can be employed to locate potential QRS complexes. By comparing the relative locations of the pace pulse and the potential QRS complex, a determination can be made as to whether the signal is likely to be a pace pulse tail. If it is, additional analysis must be undertaken before the signal can be discriminated as a pace pulse tail.

The invention discriminates pace pulse tails as those signals which follow a pace pulse signal and have an exponential decay. In order to determine whether a signal has an exponential decay, several techniques may be employed. For example, an exponentially decaying signal can be identified by calculating the ratio of the instantaneous slope to the amplitude at a series of samples along the signal following the peak of the pace pulse tail. If this ratio is approximately a constant for a predetermined time duration, then the signal must decay exponentially.

In order to increase the accuracy of the slope and amplitude measurements, the invention further includes a technique for estimating the asymptote of the pace pulse tail. An initial baseline is estimated as the point preceding the peak of the pace pulse tail which has the minimum slope. An additional correction term may also be employed for compensating for the amount of undershoot of the pace pulse tail due to the averaging effect of the high pass filter. From this estimated asymptote, it is possible to get more realistic amplitude measurements.

A threshold region above and below the asymptote may be employed to assist in the identification of the pace pulse tail. Using this region, several cases that are uncharacteristic of an exponentially decaying waveform can be defined which will not be identified as a pace pulse tail. They are: 1) signals that enter this region too close to the peak, 2) signals that enter this region and subsequently exit the region, and 3) signals that cross through this region.

The presence of 50/60 Hz power line noise may also effect the accuracy of the amplitude and slope measurements. The invention further comprises a technique for detecting and eliminating this noise. If the number of times that the difference of several consecutive samples change sign exceeds a predetermined threshold, it is possible to determine the presence of 50/60 Hz noise in the ECG signal. The 50/60 Hz noise may be removed by averaging the signal over several consecutive samples.

In addition to the aforementioned technique for identifying an ECG signal having an exponential decay, another technique can be used to identify exponentially decaying signals by matching the ECG signal to two known exponentially decaying curves. The time constant of the curves can be an average time constant for known pace pulse tails. The peak of each curve is offset from the peak of the signal by a constant. By comparing samples of the signal to the two curves, it is possible to ascertain whether the signal is bounded by the curves. Signals which are bounded by two known exponentially decaying curves, can be positively identified as decaying exponentially.

DESCRIPTION OF THE DRAWINGS

FIG. 1A is a pace pulse signal measured at the patient body surface with minimal repolarization tail, and FIG. 1C illustrates the same signal with tails being introduced by the bandpass filter in the bedside monitor.

FIG. 1B is a pace pulse signal measured at the patient body surface with repolarization tail generated by the pacemaker system, and FIG. 1D shows the same signal after the bandpass filtering at the bedside monitor.

DESCRIPTION OF THE PREFERRED EMBODIMENT

In the preferred embodiment, pace pulse tails generated by pace pulse signals are discriminated from true QRS complexes by mathematically ascertaining if the signal following the pace pulse peak has an exponential decay. Additionally, several other criteria indicative of pace pulse tails may be used to identify a signal as having an exponential decay. The description of the preferred embodiment begins by representing an exponentially decaying waveform both graphically and algebraically. From a mathematical equation, it is possible to illustrate the inventive technique for determining whether the waveform decays exponentially. Additional factors such as variations in the waveform baseline, the concept of a threshold region and 50/60 Hz noise detection and elimination are illustrated both graphically and algebraically.

Next, the method and apparatus of the preferred embodiment are disclosed, in particular, the general operation of the pace pulse tail peak detector, the asymptote estimator, threshold computation and 50/60 Hz detection and removal. Finally, the description of the preferred embodiment concludes with a description of the method for discriminating pace pulse tails.

I. Algebraic and Graphical Representation

Figure 5:
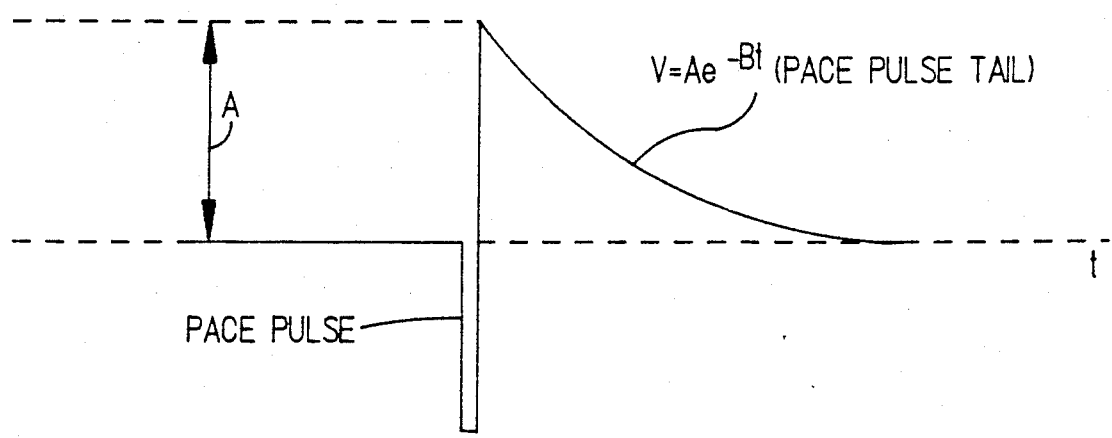
FIG. 5 is an algebraic and graphical representation of a pace pulse and an associated exponentially decaying tail of amplitude A.

FIG. 5 illustrates a pace pulse and the corresponding exponentially decaying waveform V having an amplitude A and a time constant T. This waveform is also represented by Equation 1.0. The derivative, or instantaneous rate of change of the waveform, yields the same exponentially decaying wave but attenuated by the negative time constant T, as shown in Equation 2.0. The ratio of the derivative of the signal V to itself results in a negative constant which is equivalent to the time constant of the exponential decaying waveform as shown in Equation 3.0. The relationship shown in Equation 3.0 is employed in this invention to identify the presence of a pace pulse tail.

$$V = A \, exp[-Tt] \qquad (1.0)$$

$$dV/dt = -TA \, exp[-Tt] = -TV \qquad (2.0)$$

$$(dV/dt)/V = -T \qquad (3.0)$$

Figure 6:
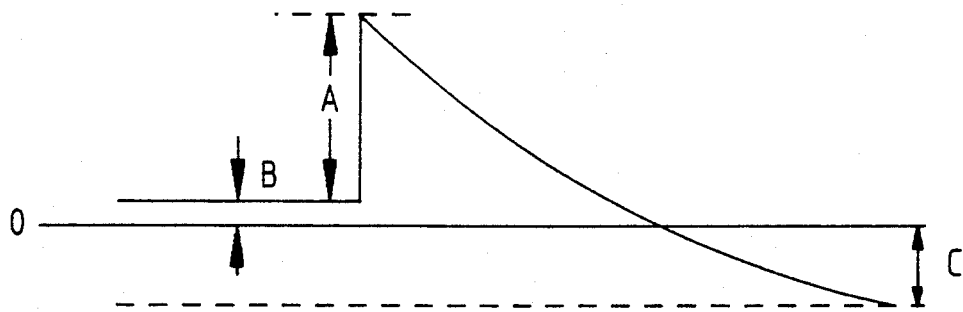
FIG. 6 is a diagram illustrating a pace pulse tail with baseline B and undershoot C.

In reality, the presence of a baseline offset and highpass filtering distorts the ECG signal. A more accurate representation of the pace pulse is depicted in FIG. 6, in which two additional components, B and C are shown. The parameter B represents the baseline offset not removed by the highpass filter. The parameter C represents the asymptote or the final resting point of the exponentially decaying waveform. This undershoot of the exponential waveform is due to the averaging effect of the highpass filter from the large pace pulse spike. Mathematically, the exponential decaying waveform shown in FIG. 6 can be modeled by Equation 4.0. The derivative of V is a function of the time constant T, offset C and V as given in Equation 5.0. The ratio of the derivative of the signal to itself given in Equation 6.0 is no longer a simple negative constant as shown in Equation 3.0. In order to utilize the relationship given in Equation 3.0 for pace pulse tail discrimination, the offset C must be estimated.

$$V = (A+B+C) \exp[-Tt] - C \quad (4.0)$$

$$dV/dt = -T(A+B+C)\exp[-Tt] = -T(V+C) \quad (5.0)$$

$$(dV/dt)/V = -T(1+C/V) \quad (6.0)$$

Figure 7:
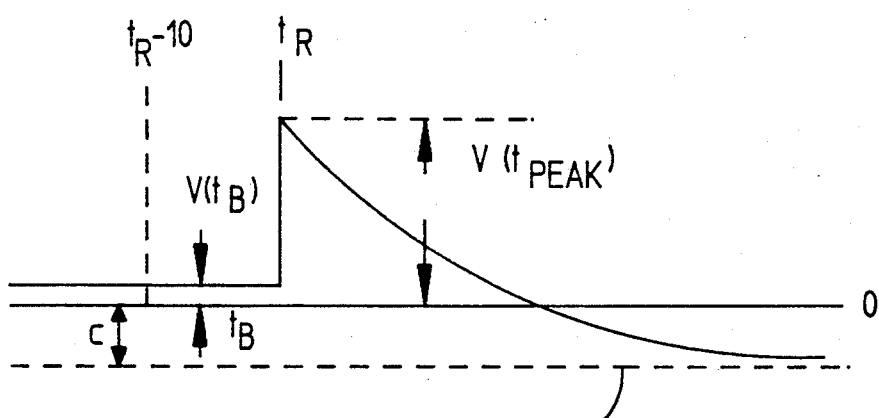
FIG. 7 illustrates the relationship of the asymptote to the baseline and the peak signal value.

FIG. 7 illustrates how the asymptote can be estimated. First, an initial baseline estimate is determined by locating the point $t_B$ with the minimum slope within a predefined search window. The search window located immediately prior to the peak of the pace pulse tail at $t_R$, is 80 msec wide, which is 10 data samples at a sampling rate of 125 samples per second. Mathematically, the baseline estimate is represented as follows:

$$B = V(ts) \quad (7.0)$$

Where $$t_B = \text{ARG}[\text{MIN } \{\text{ABS}[V(t) - V(t-1)], \ t \ \epsilon [t_R - 10, t_R]\}] \quad (8.0)$$

The final asymptote estimate as shown in Equation 9.0 is the sum of the initial baseline estimate plus a correction term.

$$= V(t_B) - \frac{1}{8}[V(t_{PEAK}) - V(t_B)] \quad (9.0)$$

The correction term is used to estimate the amount of undershoot of the exponential waveform. This ensures that the baseline is correctly positioned relative to the asymptote of the exponential wave. A correction value of one-eighth of the adjusted peak amplitude which is the difference of the peak amplitude $V(t_{PEAK})$ and the initial baseline estimate $V(t_B)$, has been empirically determined to provide the most accurate estimate.

Figure 8:
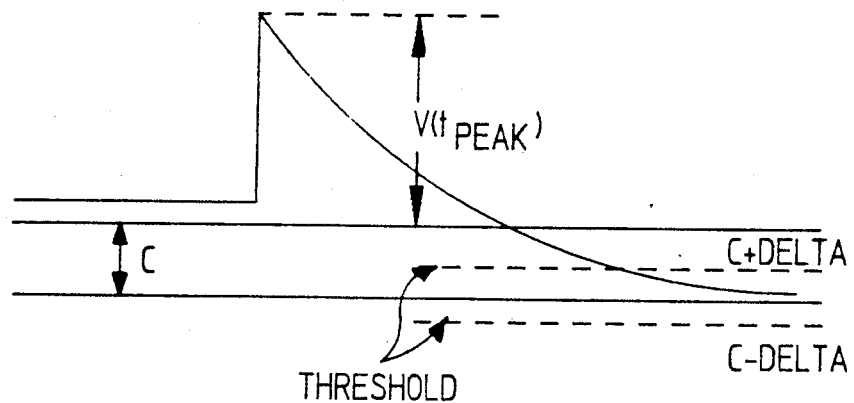
FIG. 8 is a diagram illustrating an exponentially decaying waveform entering into a threshold region.
Figure 9:
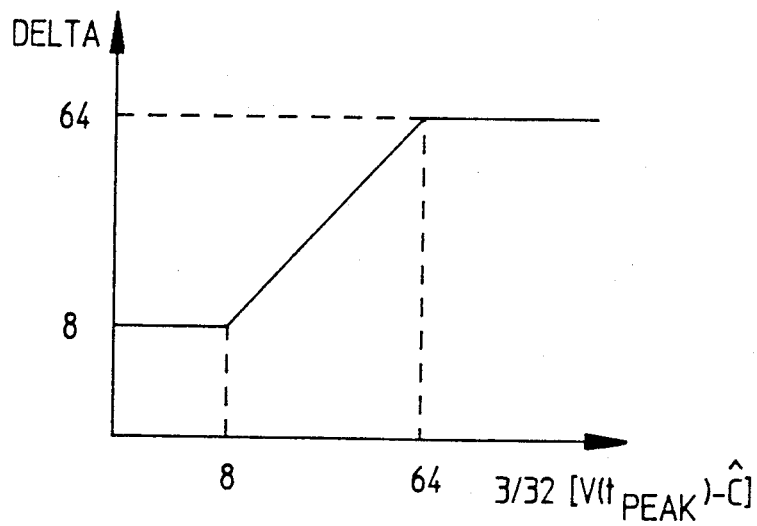
FIG. 9 is a diagram illustrating how the threshold region is calculated.

FIG. 8 illustrates the construction of a threshold region around the asymptote of the pace pulse tail. This region which is centered around the asymptote is bounded between +Delta and −Delta. The threshold Delta is computed in Equation 10.0 and is illustrated in FIG. 9. The value of Delta is between a minimum value of 8 and a maximum value of 64, both of which are empirically determined Within these limits the value of Delta is directly proportional to the adjusted peak amplitude of the pace pulse tail.

$$DELTA = MIN\{64, MAX[3/32 \ [V(t_{PEAK}) - C], 8]\} \quad (10.0)$$

Once a signal enters into this region it does not have to meet the relationship given in Equation 3.0 for it to be considered as an exponential decay signal as long as the signal stays in this region.

Figure 10:
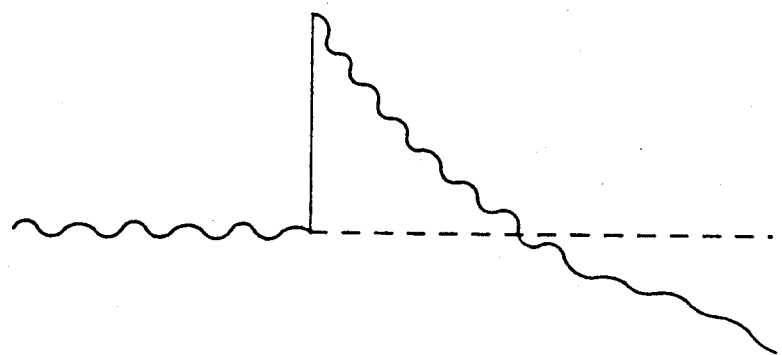
FIG. 10 is a diagram illustrating the effects of 50/60 Hz noise on an exponentially decaying waveform.

If the signal contains any power line noise, it can be represented as an additive sinusoidal signal as shown in Equation 11.0 and illustrated in FIG. 10. The ratio of the derivative to the signal amplitude V (which are shown in Equation 12.0 and 13.0), are not constant. Therefore it is clear that the success of the inventive technique is enhanced by the removal of any power line noise.

$$V = A \exp[-Tt] + F \sin(wt) \quad (11.0)$$

$$dV/dt = TA \exp[-Tt] + Fw \cos(wt) \quad (12.0)$$

$$(dV/dt)/V = -T + (F/V)[T \sin(wt) + w \cos(wc)] \quad (13.0)$$

II. Method and Apparatus of the Preferred Embodiment

Figure 11:
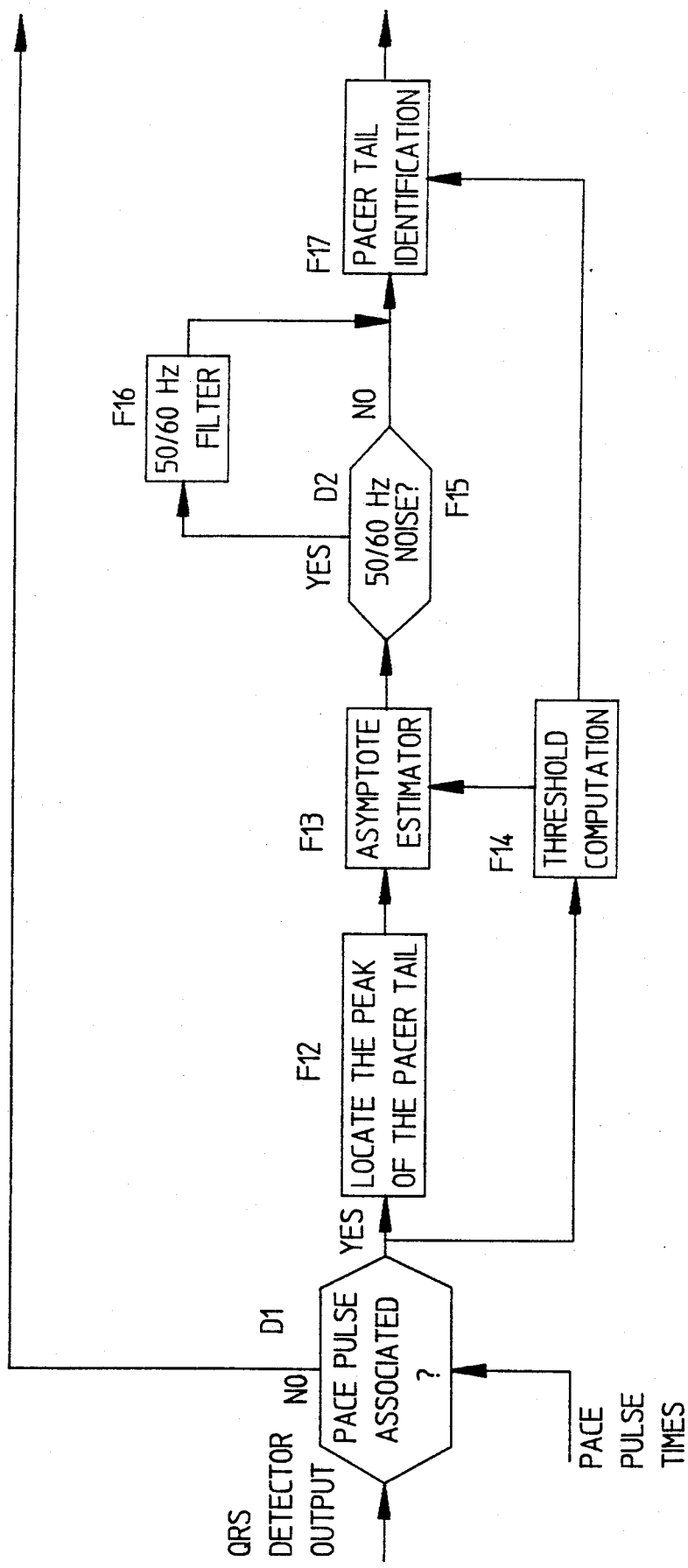
FIG. 11 is a block diagram illustrating the preferred embodiment of the invention.

The block diagram of FIG. 11 illustrates the inventive method for discriminating pace pulse tails. In order to identify pace pulse tails, the corresponding pace pulse signal is first located. Although the pace pulse signal does not have to be removed, pace pulse tail discrimination can be enhanced by such removal.

Figure 2A:
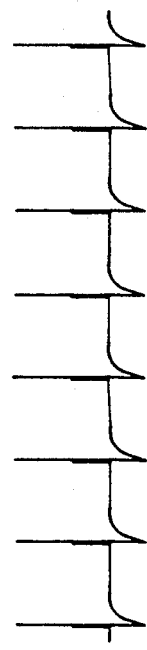
FIG. 2A illustrates a pace pulse signal with pace pulse tail.
Figure 2B:
FIG. 2B illustrates the remaining pace pulse tail, after the pace pulse has been removed.
Figure 3:
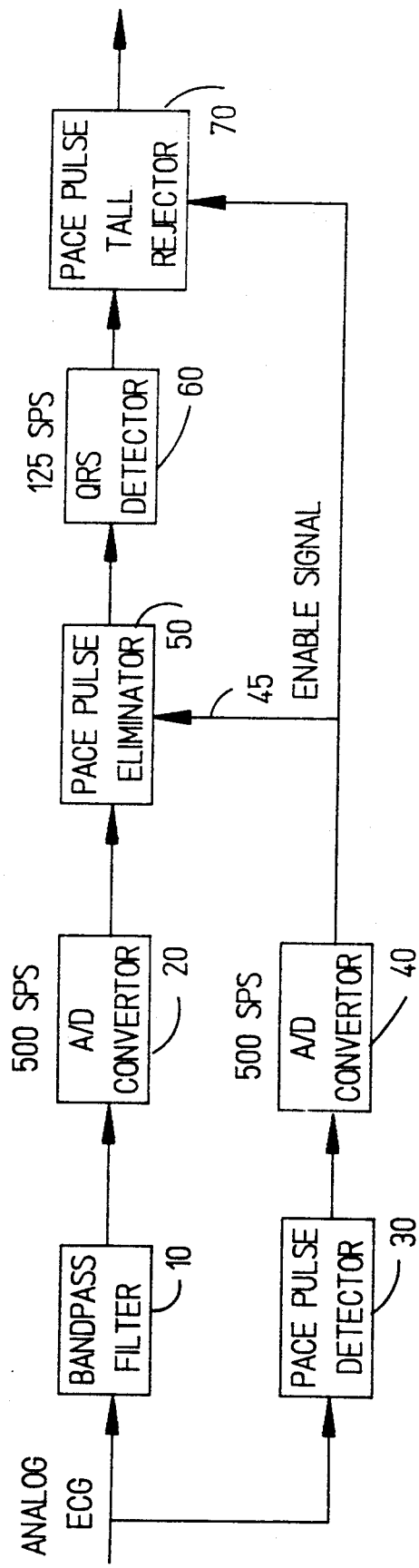
FIG. 3 is a block diagram of the prior art device employed for identifying and removing pace pulses.
Figure 4:
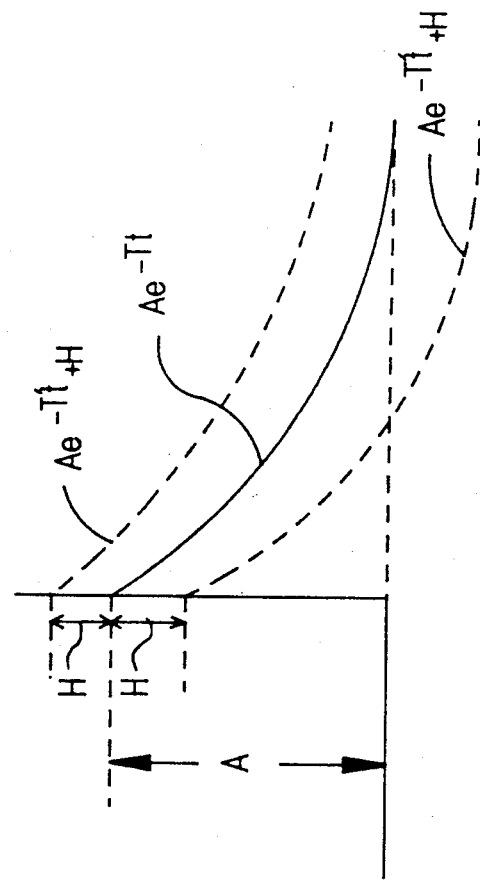
FIG. 4 is a diagram illustrating a curve fitting technique for identifying a pace pulse tail.

In this regard, the prior art method and apparatus highlighted in FIG. 3 is employed. In particular, a band pass filter 10 is employed to eliminate unwanted signals due to baseline wander and high frequency muscle artifacts. An A/D converter 20 is used to digitize and sample the filtered ECG signal at a rate of 500 samples per second. While the band pass filter removes unwanted signals, it may also generate exponentially decaying tails due to pace pulses. In parallel with the band pass filter 10 is a pace pulse detector 30 and another A/D converter 40 which are employed to locate the pace pulse and to generate a corresponding enable signal 4 which is employed to synchronize a pace pulse eliminator 50. The pace pulse eliminator 50, described in U.S. Pat. No. 4,832,041, receives the filtered and digitized ECG signal and eliminates the pace pulse. The elimination of the pace pulse results in a gap being formed which is "filled" by approximating a line where the pace pulse used to be. A QRS detector 60 is coupled to the output of the pace pulse eliminator 50 for detecting the presence of QRS complexes after pace pulses have been removed. The ECG samples used by the QRS detector is 125 samples per second.

Figure 12:
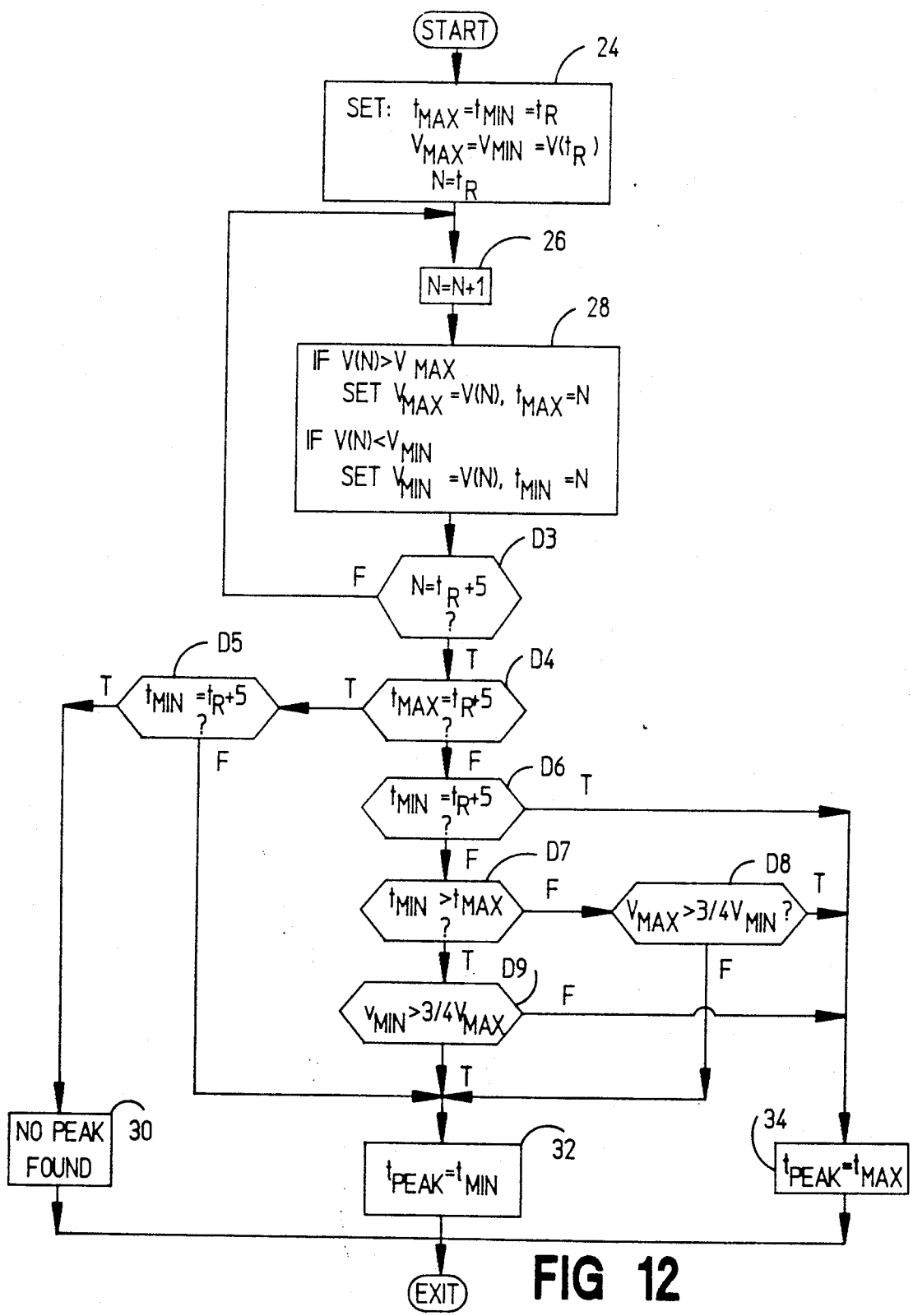
FIG. 12 is a flowchart setting forth the method steps for identifying the peak of a pace pulse tail.

The present invention is embodied in the pace pulse tail rejector 70 which is coupled to the output of both the A/D converter 40 and the QRS detector 60. Thus the input to the pace pulse tail rejector 70 is the ECG waveform from the pace pulse eliminator. The pace pulse detector 30 provides an enable signal which indicates the presence of a pace pulse. The general operation of the pace pulse tail rejector 70 is shown functionally in the block diagram illustrated in FIG. 11. The following flowcharts correspond to each block in the diagram; FIG. 12—Pacer Tail Peak Detector, FIG. 13—Asymptote Estimator, FIG. 14—Threshold Computation, FIGS. 15 and 16—50/60 Hz Noise Detector and Filter, and FIG. 17—Pace Pulse Tail identification. The first step in ascertaining whether the output of the QRS Detector 60 is a pace pulse tail is illustrated in FIG. 11 where a determination must be made to see if the signal is preceded by a pace pulse (D1). If there is no pace pulse within a predetermined distance of the potential QRS complex, then this signal cannot be identified as a pace pulse tail.

If the signal is pace pulse associated, then the peak of the pac pulse tail is located (F12) using the technique set forth in FIG. 12. In particular, a signal maximum (Vmax) and a signal minimum (Vmin) are determined over a predetermined period (at 26,28 and D3), and if Vmax is greater than ¾ times Vmin, then Vmax is the peak of the pace pulse tail (at D8 and 34), or if Vmin is greater than ¾ times Vmax, then Vmin is the peak of the pace pulse tail (at D9 and 32). If Tmax equal Tmin, then no peaks are found.

Figure 13:
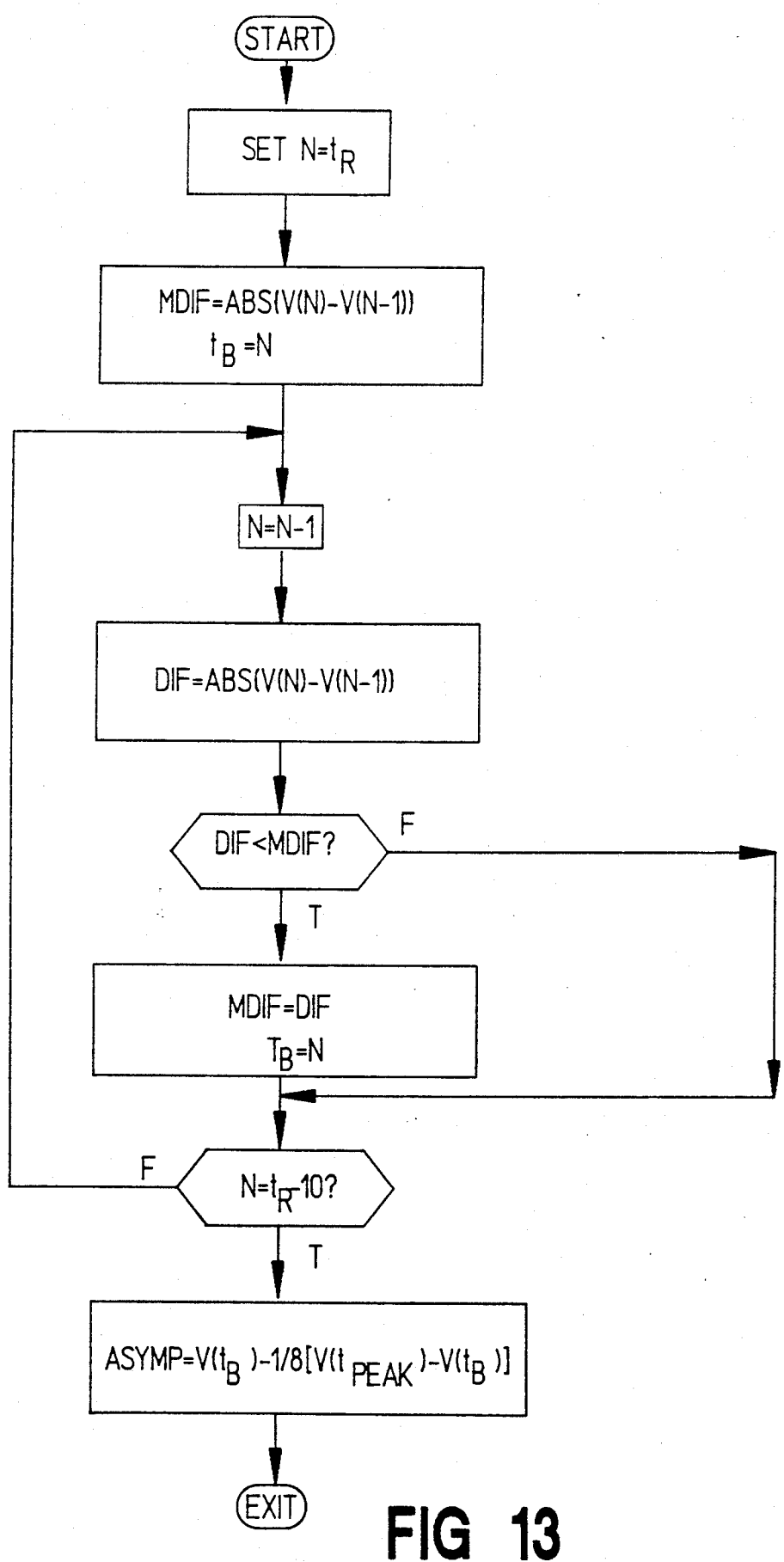
FIG. 13 is a flowchart setting forth the method steps for estimating the asymptote.

The next step in the process as set forth in the block diagram of FIG. 11, is to make an asymptote estimation (F13). The flowchart of FIG. 13 illustrates how the asymptote is estimated. Empirical studies have shown that an accurate estimate of the asymptote is equal to:

$$ASYMP = V(t_B) - \frac{1}{2}[V(t_{PEAK}) - V(t_B)]$$

where $V(t_B)$ is the initial baseline estimate given in Equations 7.0 and 8.0, and $V(t_{PEAK})$ is the peak signal determined using the technique set forth in FIG. 12.

A threshold region is established on either side of the estimated asymptote. The manner in which the decaying signal enters and possibly crosses through this region is important to how it is classified. For example, if an ECG signal enters the threshold region too rapidly, or if it enters and comes out again or if it enters and passes right through, then the signal will not be identified as a pace pulse tail as this is not characteristic of an exponentially decaying signal which continually approaches the asymptote. As set forth in FIG. 11 the threshold computation is made after the asymptote estimation and prior to the identification of the pace pulse tail.

Figure 14:
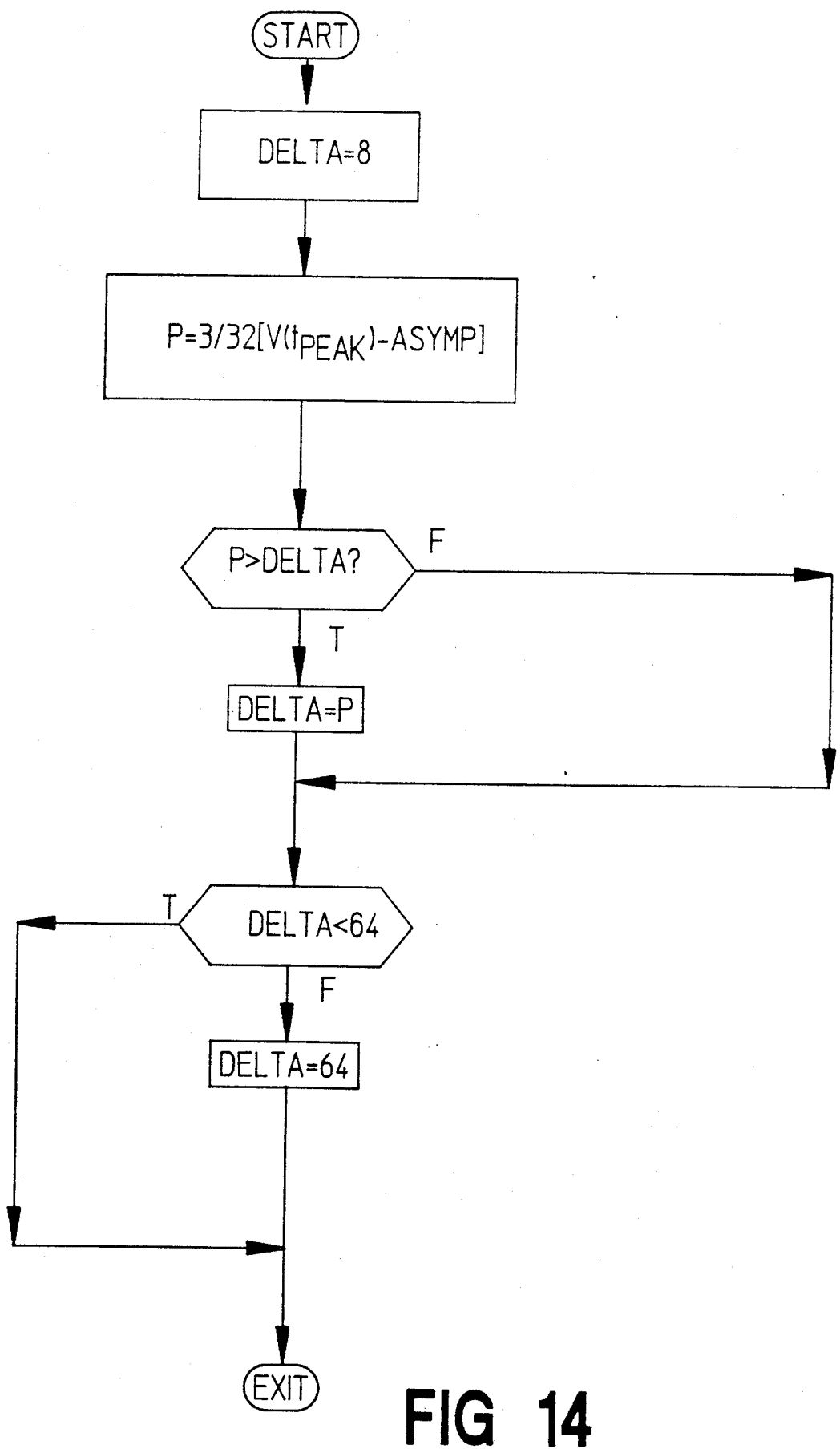
FIG. 14 is a flowchart setting forth the method steps of making a threshold computation.
Figure 15:
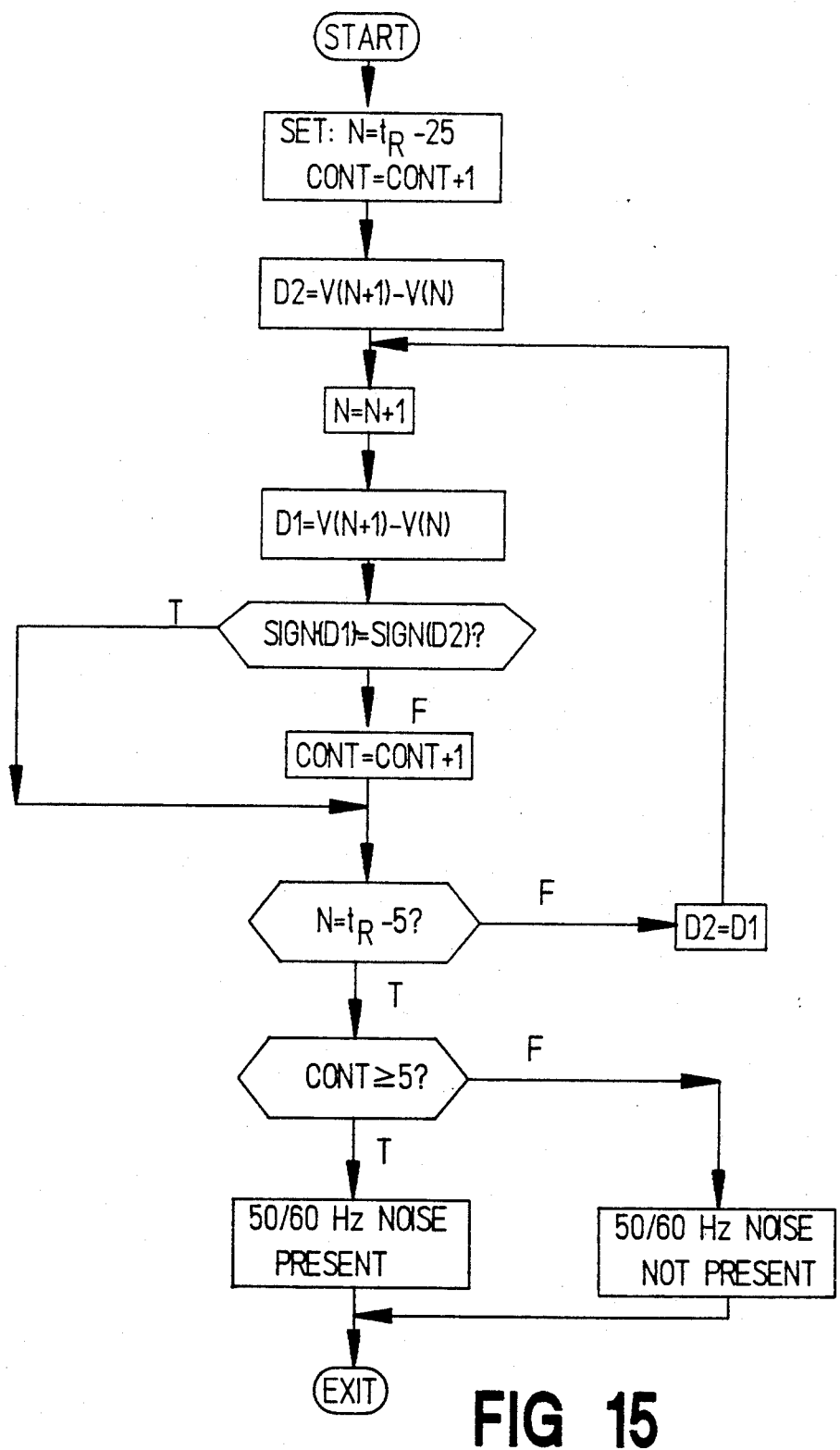
FIG. 15 is a flowchart setting forth the method steps for detecting 50/60 Hz noise.

The flowchart of FIG. 14, illustrates how the threshold is calculated using the formula given in Equation 10.0.

The presence of noise may effect the ability of the invention to accurately discriminate pace pulse tails. In particular, 50/60 Hz noise has been found to cause erroneous slope measurements. The flowchart of FIG. 15 highlights how this noise may be detected. In order to detect the presence of this noise, the differences of consecutive samples of the ECG signal, approximately 200 milliseconds to 40 milliseconds preceding the detector peak are compared. The number of times that these differences change sign are counted and used as an estimate of the number of noise cycles contained in the window. If the number of cycles is greater than 5 in a 160 millisecond window, then 50/60 cycle noise is present.

Figure 16:
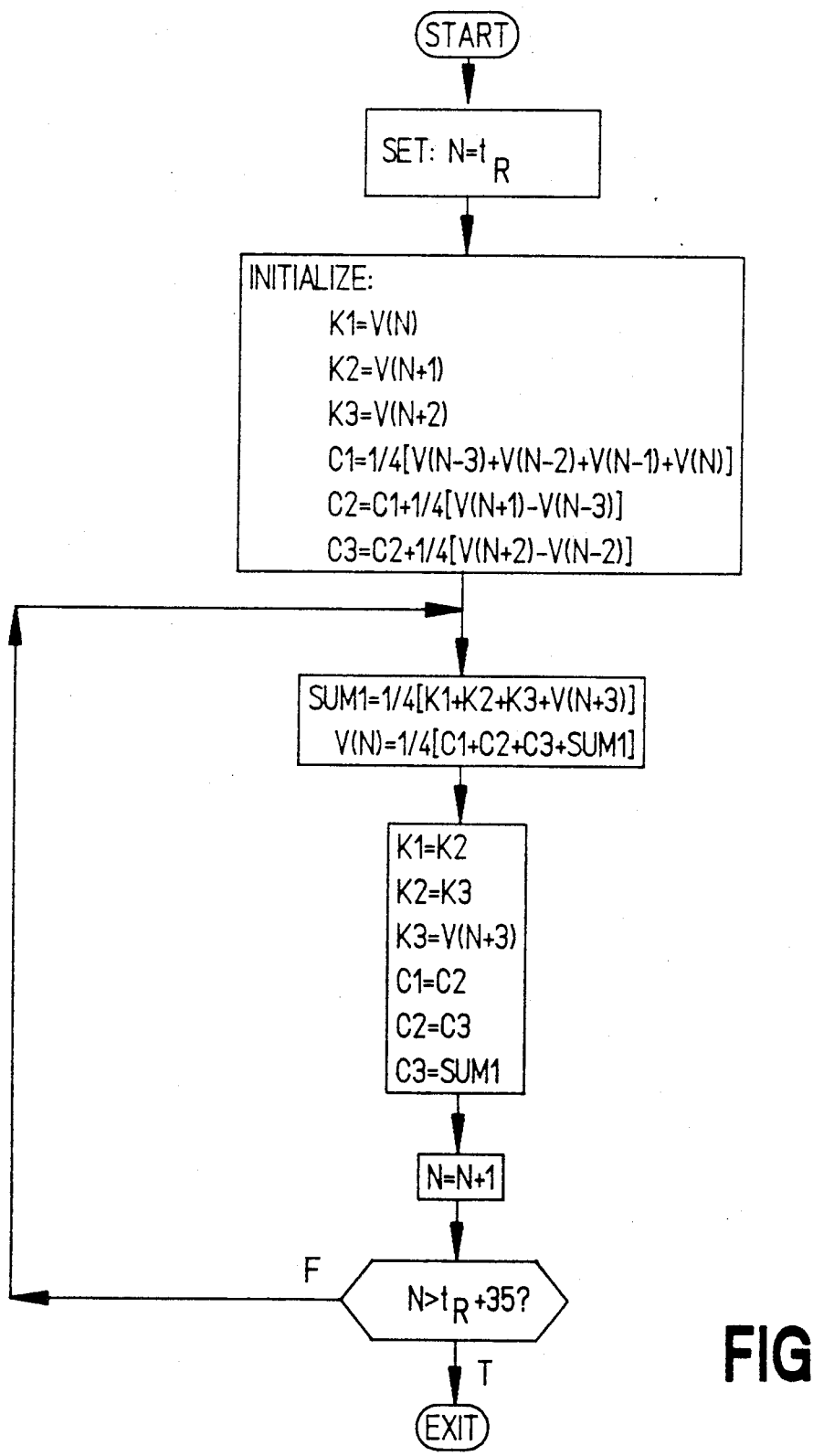
FIG. 16 is a flowchart setting forth the method steps for removing 50/60 Hz noise.

The flowchart of FIG. 16 highlights how this noise may be removed. In order to remove 50/60 Hz noise, a filtering "window" of four consecutive points is utilized to compute the average amplitude of the series of samples Once a value has been determined, the window is shifted by one, and four amplitude values in the window are averaged providing a second averaged amplitude value. This process is continued for 25 samples, and then the process is repeated a second time to ensure that the 50/60 Hz noise is removed.

III. Method for Discriminating Pace Pulse Tails

Figure 17:
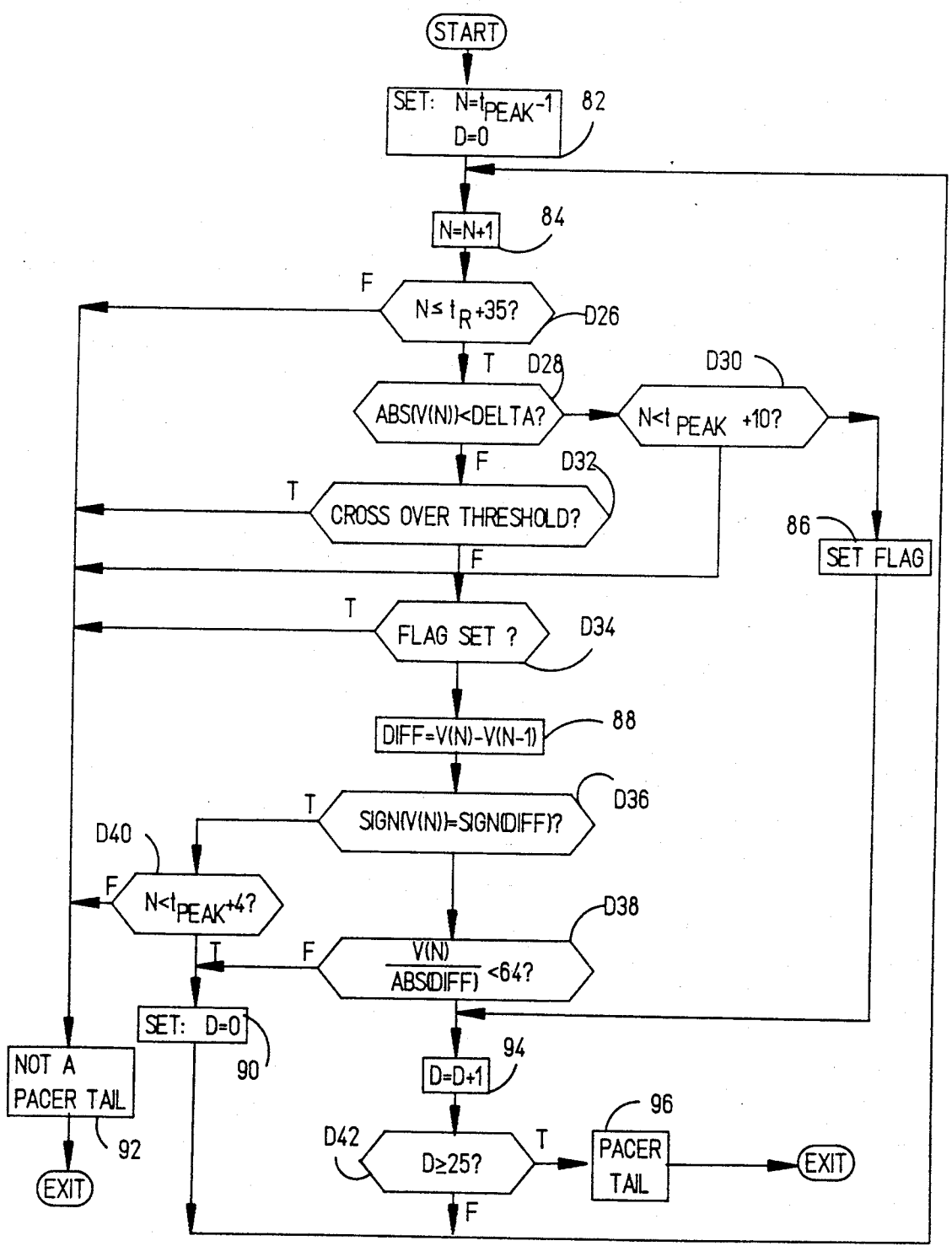
FIG. 17 is a flowchart setting forth the method steps of the preferred embodiment of the invention for discriminating pace pulse tails.

The preferred method for ascertaining whether a signal has an exponential decay is set forth in the flowchart FIG. 17. In determining whether the signal decays exponentially, ratios of the instantaneous slope to the amplitude of a series of ECG signal samples are computed. An exponential waveform is identified when this ratio for each sample is the same. It should be noted that no single constant can be selected to represent all types of pace pulse tails, therefore, any ratio that falls within a small predetermined range of negative values will be associated with an exponentially decaying waveform. Ratios having a positive value indicate a departure from the exponential waveform shape unless they occur within a short period from the start of the window, or if the ECG signal is near the asymptote at which point it is very susceptible to noise.

As set forth in the flowchart of FIG. 17, the preferred embodiment employs a search window of 35 samples following the peak of the exponential waveform to determine if the ECG signal decays exponentially. Prior to conducting the ratio analysis, events may occur which are not characteristic of an exponentially decaying waveform and obviate the need for such an analysis. In particular, if the ECG signal amplitude is less than the threshold value within 10 samples of the waveform peak (at D30, "N<Tpeak+10"), then the ECG signal can not be identified as a pace pulse tail as it has "decayed" faster than a typical exponential decaying waveform. On the other hand, if it is outside the 10 sample window, then a flag is set (at 86, "Set Flag") indicating that this particular sample is presently within the threshold and the next sample may be analyzed (at 9 4, "D=D+1"). If on the other hand, the amplitude is greater than the threshold value (decision point D28), then, prior to the ratio analysis, the voltage level must be checked to see if it has crossed through the threshold value to the other side (decision point D32). This is not characteristic of an exponentially decaying waveform and therefore should not be identified as a pace pulse tail. If the ECG signal has not crossed through the threshold, but the flag is set (decision point D34), indicating that on a previous sample the ECG signal has already entered the threshold region, then the signal should not be identified as a pace pulse tail. This is true as an exponential waveform, once in the threshold region, must stay there.

Assuming the flag is not set, then the slope at that particular point is calculated (at 88, "DIFF=V9N0−V(n−1)"). Next a decision must be made as to whether the sign of the slope is the same as the sign of the amplitude at that point ( decision point D36, "Sign[x(n)]=Sign(Delta)"). In general, the signs should always be different, if not, then the signal is either not a pace pulse tail, or, if less than 4 samples have been taken (decision point D40, "n<Tpeak+4") the process was started at a false wave peak and the counter should be initialized and the process restarted (at 90, "D=Q").

Assuming that the amplitude and the slope have the same sign and the ratio of the amplitude and the slope is greater than 0 and less than 64 (decision point D38), then the criteria for a point on an exponential waveform have been met and the counter is incremented by 1 (at 94, "D=D+1") and if the total count is greater than or equal to 25 (decision point D42), indicating that the ratio of the amplitude and the slope has been less than 64 for at least 25 points, the signal is identified as a pace pulse tail (at 96). If the total count does not equal 25, then N is incremented by one (at 84, N=N+1), and the next sample is analyzed.

Although best results are obtained by the forgoing pace pulse tail rejection method and apparatus, changes and modification of the invention, as set forth in the specifically described embodiments, can be carried out without departing from the scope of the invention which is intended to be limited only by the scope of the appended claims. For example, the curve fitting technique described in the summary is another acceptable method for determining whether or not a signal decays exponentially.

We claim:

1. A method for discriminating a pace pulse tail from a QRS complexe in an ECG signal, comprising the following method steps;
   locating the peak of the pace pulse tail;
   detecting a signal following the peak;
   determining if the detected signal decays exponentially; and
   discriminating the detected signal as a pace pulse tail if it decays exponentially.

2. The method of claim 1, wherein the method step of determining if the detected signal decays exponentially further comprises the steps of;
   calculating the instantaneous slope of the detected signal at a series of sample points following the peak;
   dividing the slope of the detected signal by the signal amplitude at each corresponding sample point; and
   identifying the detected signal as having an exponential decay when the ratio at each sample point is within a predetermined range.

3. The method of claim 2, wherein the detected signal is identified as a pace pulse tail if an exponential decay persists for a duration of at least 200 msec following the peak.

4. The method of claim 2, wherein the method step of identifying a detected signal as a pace pulse tail further comprises the step of computing an estimate of the asymptote of the pace pulse tail.

5. The method of claim 4, wherein a bounded threshold region is established above and below the estimated asymptote, and signals are not identified as pace pulse tails if they enter and subsequently exit the bounded region.

6. The method of claim 5, wherein signals are not identified as a pace pulse tail if they cross the threshold within approximately 80 milliseconds from the pace pulse peak.

7. The method of claim 5, wherein the threshold region is defined as being bounded by two lines a distance A from either side of the estimated asymptote, where $A = 3/32[V(t_{PEAK}) - \text{Asymptote Estimate}]$.

8. The method of claim 4, wherein the asymptote estimate is calculated by taking an initial baseline estimate defined as the horizontal line passing through the point, just prior to the peak of the pace pulse tail, having minimum slope and subtracting an additional adjustment value, corresponding to approximately one-eighth of the difference between the peak of the pace pulse tail and the initial baseline estimate.

9. The method of claim 2, wherein the method of identifying a detected signal as a pace pulse tail further comprises the step of removing 50/60 Hz noise from the input signal.

10. The method of claim 9, wherein the step of removing 50/60 Hz noise further comprises the steps of:
    identifying the presence of 50/60 Hz noise when the number of times that the difference of several consecutive samples changes sign, exceeds a predetermined threshold; and
    removing the 50/60 Hz noise by averaging the amplitude of a series of consecutive samples.

11. The method of claim 1, wherein the method step of determining if the detected signal decays exponentially further comprises the steps of:
    Generating two exponential curves in accordance to:

$$Ae^{-T_3 t} + F \text{ and } Ae^{-T_3 t} - F$$

where A is equal to the amplitude of the detected signal t is equal to time, F is a constant and $T_3$ is an empirically determined time constant corresponding to the average value of time constants for known pace pulse tails;
    comparing samples of the detected signal and said generated curves to determine whether said detected signal is bounded by said curves;
    identifying the detected signal as having an exponential decay if it is bounded by said curves.

* * * * *